United States Patent [19]

Guzzi et al.

[11] Patent Number: 5,312,961
[45] Date of Patent: May 17, 1994

[54] 2-AMINO-7-HYDROXYTETRALIN CARBOXYLALKYL ETHERS

[75] Inventors: Umberto Guzzi; Roberto Cecchi, both of Milan; Luciano Manara, Alessandria, all of Italy

[73] Assignee: Elf Sanofi, Paris, France

[21] Appl. No.: 905,483

[22] Filed: Jun. 29, 1992

Related U.S. Application Data

[63] Continuation of Ser. No. 622,964, Dec. 6, 1990, abandoned, which is a continuation-in-part of Ser. No. 480,207, Feb. 14, 1990, abandoned.

[30] Foreign Application Priority Data

Feb. 14, 1989 [FR] France .................... 89 01910
Jun. 12, 1990 [EP] European Pat. Off. ........ 90401606.0

[51] Int. Cl.$^5$ .......................................... C07C 101/72
[52] U.S. Cl. ..................................................... 560/45
[58] Field of Search ............................................ 560/45

[56] References Cited

U.S. PATENT DOCUMENTS 4,921,998  5/1990  Niewhoner et al. .................. 560/45
4,954,504  9/1990  Chen et al. ........................... 514/265

FOREIGN PATENT DOCUMENTS 0040915  3/1984  European Pat. Off. .
0254545  1/1988  European Pat. Off. .
0255415  2/1988  European Pat. Off. .
0257378  3/1988  European Pat. Off. .
0258095  3/1988  European Pat. Off. .
0267878  5/1988  European Pat. Off. .
0277917  10/1988  European Pat. Off. .

OTHER PUBLICATIONS

De Wied, Ed., *European Journal of Pharmacology*, 100, Nos. 3-4, 1984, pp. 309-319.
Wilson et al., *Journal of Cardiovascular Pharmacology*, 6, No. 6, Nov./Dec. 1984, pp. 1216-1221.
Manara et al., *Fidia Research Foundation Symposium Series*, 2, May 1989, pp. 131-147.
Forth et al., Ed., *Pharmakologie und Toxikologie*, 1983, 4th edition, pp. 94-95.
Wilson et al., *Life Sciences*, 35, No. 12, Sep. 1984, pp. 1301-1309.

*Primary Examiner*—José G. Dees
*Assistant Examiner*—Samuel Barts
*Attorney, Agent, or Firm*—Bacon & Thomas

[57] ABSTRACT

The invention relates to 2-amino-7-hydroxytetralin carboxyalkyl ethers of formula

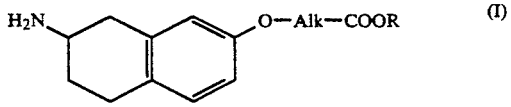

wherein Alk represents a straight or branched ($C_3$-$C_5$)alkylene group, and R is hydrogen or ($C_1$-$C_4$)alkyl, useful as starting materials in the synthesis of 7-substituted phenylethanolaminotetralins of formula (XII)

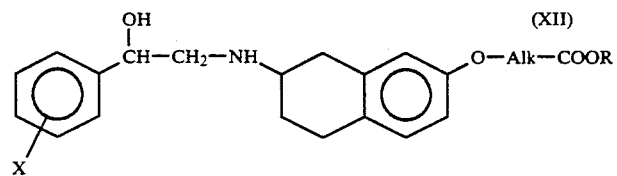

wherein X represents hydrogen, halogen, ($C_1$-$C_4$)alkyl, or trifluoromethyl which are useful as spasmolytics and anti-glaucoma agents.

The new 7-substituted phenylethanolaminotetralins (XII) as well as the intermediates in the preparation of the compounds (I), the N-protected 2-amino-7-hydroxytetralin carboxyalkyl ethers, are also claimed.

4 Claims, No Drawings

2-AMINO-7-HYDROXYTETRALIN CARBOXYLALKYL ETHERS this application is a continuation of application Ser. No. 07/622,964, filed Dec. 6, 1990, now abandoned, which is a continuation-in-part of application Ser. No. 07/480,207, filed Feb. 14, 1990, now abandoned.

The present invention relates to 2-amino-7-hydroxytetralin carboxyalkyl ethers, to a process for the preparation thereof and the intermediates in said process, to the use of said ethers as starting materials in the synthesis of pharmacologically active compounds and to the new 7-substituted phenylethanolaminotetralins endowed with spasmolytic and antiglaucoma activity thus obtained.

More particularly, in one of its aspects, the present invention concerns 2-amino-7-hydroxytetralin carboxyalkyl ethers of the following formula

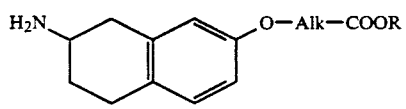

wherein
- Alk represents a straight or branched $(C_3-C_5)$alkylene group, and
- R represents hydrogen or $(C_1-C_4)$alkyl, and their salts.

More particularly, the term Alk may represent

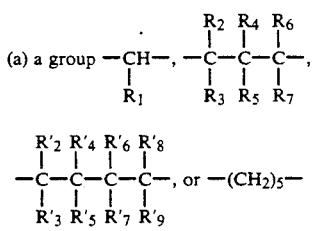

wherein
- $R_1$ is ethyl, propyl or butyl,
- $R_2$ to $R_7$ are all hydrogen atoms or one of $R_2$ to $R_7$ is a methyl or ethyl group and the others are hydrogen atoms, or two of $R_2$ to $R_7$ are methyl groups and the others are hydrogen atoms;
- $R'_2$ to $R'_9$ are all hydrogen atoms or one of $R'_2$ to $R'_9$ is a methyl group and the others are hydrogen atoms;

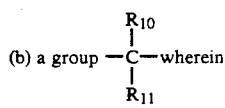

- $R^{10}$ and $R_{11}$ are independently methyl or ethyl or $R_{11}$ is also propyl when $R_{10}$ is methyl;

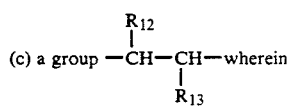

- one of $R_{12}$ and $R_{13}$ is hydrogen and the other is methyl, ethyl or propyl, or one of $R_{12}$ and $R_{13}$ is methyl and the other is methyl or ethyl.

The new compounds are useful as starting materials in the preparation of pharmacologically active compounds, in particular 7-substituted phenylethanolaminotetralins with spasmolytic and antiglaucoma activity.

As used herein the term "tetralin" stands for 1,2,3,4-tetrahydronaphthalene and the term "2-tetralone" for the corresponding 2-oxo derivative.

The compounds of above formula (I) and their salts can be prepared by the following general method, which represents a further specific object of the present invention and which comprises:

(A) submitting a N-protected 2-amino-7-hydroxytetralin of formula (II)

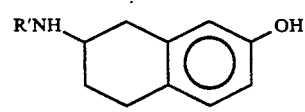

wherein
- R' is an amino-protecting group which may suitably be removed by catalytic hydrogenation or mild acidic hydrolysis, to a carb(alk)oxyalkylation reaction with a compound of formula (IIIa)

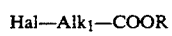

wherein R is as defined above, Hal represents chloro, bromo or iodo, and $Alk_1$ represents an alkylene group as defined under (a) above, in the presence of a basic condensation agent,
or with a compound of formula (IIIb)

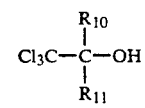

wherein $R_{10}$ and $R_{11}$ are as defined above under (b) above, in the presence of a strong base, optionally followed by reaction of the obtained product with thionyl chloride in the suitably selected $(C_1-C_4)$alkanol,
or with a compound of formula (IIIc)

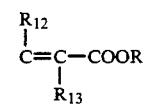

wherein R, $R_{12}$, and $R_{13}$ are as defined under (c) above, optionally in the presence of catalytic amounts of a quaternary ammonium hydroxide, to obtain a N-protected 2-amino-7-hydroxytetralin carboxyalkyl ether of formula (IV)

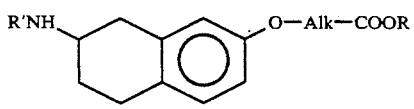

wherein R', Alk, and R are as defined above, and
(B) removing the N-protecting group by catalytic hydrogenation or mild acidic hydrolysis and, after optional saponification of the lower carbalkoxy group to carboxy, isolating the compound of formula (I), as the free base or as a salt thereof, and optionally converting it into one of its salts.

The term "carb(alk)oxyalkylation" typically identifies a condensation reaction of the phenol hydroxy group with a reactant which is capable of etherifying said hydroxy group with an alkyl group substituted with a carb(alk)oxy group, i.e. a carboxy or carbalkoxy group, wherein the term "carbalkoxy" designates a $(C_1-C_4)$alkoxycarbonyl group.

Preferred N-protecting groups include tert-butoxycarbonyl (Boc), benzyloxycarbonyl and in general those N-protecting groups which are conventionally employed in peptide chemistry, or benzyl, benzhydryl, or trityl groups, either unsubstituted or substituted in the benzene ring by a methoxy group.

As starting compounds of formula (IIIa), alkyl bromoalkanoates are preferably employed. The reaction between the N-protected 2-amino—7-hydroxytetralin (II) and the compound (IIIa) is carried out in an organic solvent such as acetone, ethyl acetate, or tetrahydrofuran, using a conventional basic condensation agent such as an alkaline carbonate, typically potassium carbonate.

For the preparation of the compounds of formula (I) wherein Alk is a group —$C(R_{10}R_{11})$—, compounds of formula (IIIb) are reacted with the N-protected 2-amino-7-hydroxytetralin (II), according to the general method described in J. Am. Chem. Soc., 1948, 70, 1153–1158. In this case the reaction is preferably carried out in the presence of a strong base, such as sodium or potassium hydroxide, and when a compound of formula (I) is desired wherein R is different from hydrogen, the obtained acid is treated with thionyl chloride in the suitably selected alkanol.

The reaction between the N-protected 2-amino-7-hydroxytetralin (II) and the acrylic acid derivatives of formula (IIIc) may be carried out either in the absence or in the presence of an inert, apolar, organic solvent such as benzene, toluene, ethyl ether, methylene chloride, and the like. The reaction may be catalyzed, if desired, by small amounts of a quaternary ammonium hydroxide, e.g. trimethylbenzylammonium hydroxide. Preferably, to avoid addition of the acrylate to the amino-tetralin bond, when using a reactant of formula (IIIc), the amino group of the reaction partner (II) is protected with Boc or any other easily removable urethane-type protecting group.

The thus obtained N-protected 2-amino-7-hydroxytetralin carboxyalkyl ether of formula (IV) is recovered by standard methods well known to chemists, optionally as a salt thereof, and is then subjected to deprotection.

Removal of the N-protecting group is accomplished by catalytic hydrogenation or mild acidic hydrolysis according to methods well known in the literature. In particular the Boc group is readily cleaved under mild acidic conditions, by the action of trifluoroacetic acid. The other groups listed above are removed by catalytic hydrogenation, preferably using Pd/C as the hydrogenation catalyst. The trityl and methoxy-trityl groups may be removed also by hydrolysis under mild acidic conditions, e.g. with 50% formic acid or with hydrogen chloride in an organic solvent.

To afford the corresponding free carboxylic acids, the compounds of formula (I) may be saponified, either before or after deprotection of the amino group.

The compounds of formula (I) are isolated by conventional methods, preferably as the corresponding addition salts with mineral or organic acids which allow a suitable separation or crystallisation of the compounds (I), such as for instance picric acid, oxalic acid, or with an optically active acid, e.g. a mandelic or camphorsulfonic acid, or with mineral or organic acids that form pharmaceutically acceptable salts such as the hydrochloride, hydrobromide, sulfate, hydrogensulfate, dihydrogenphosphate, methanesulfonate, methylsulfate, maleate, fumarate, naphthalenesulfate, and the like.

The free base may be obtained by neutralization, and converted into another acid addition salt or, when R is hydrogen, into a metal salt thereof, typically an alkaline salt, such as the sodium salt, by conventional procedures.

The N-protected 2-amino-7-hydroxytetralins of formula (II) may be prepared starting from 2-amino-7-hydroxy-tetralin of formula (IIa)

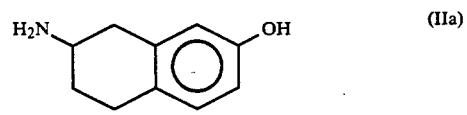

or directly from 7-methoxy-2-tetralone of formula (V)

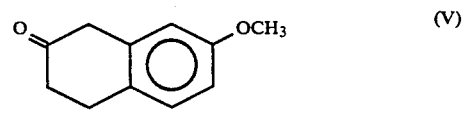

In its turn, 2-amino-7-hydroxytetralin (IIa) may be prepared starting from the corresponding methoxytetralone of formula (V) through reaction with benzylamine, reduction with sodium borodydride of the thus obtained benzylimino intermediate, removal of the benzyl group by catalytic hydrogenation and demethylation with 48% hydrobromic acid according to following Scheme 1:

SCHEME 1

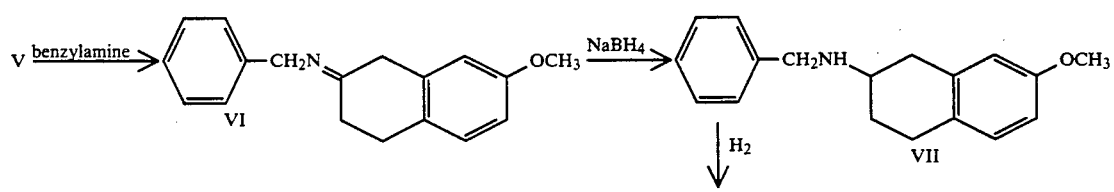

-continued
SCHEME 1

[Structures IIa and VIIa shown, with HBr conversion from VIIa (OCH3) to IIa (OH)]

The reaction of the compound of formula (V) with benzylamine is carried out, according to the conventional methods for the preparation of Schiff's bases, in an organic solvent such as toluene, in the presence of p-toluenesulfonic acid. The thus obtained compound (VI) may then be reduced, without being isolated or purified, with sodium borohydride. Catalytic hydrogenation of said compound, e.g. with Pd/C, affords 2-amino-7-methoxytetralin of formula (VIIa) which is heated in 48% hydrobromic acid yielding 2-amino-7-hydroxytetralin (IIa) hydrobromide readily converted into the free base by neutralisation.

In the first step of above Scheme 1 leading to the N-protected intermediate, benzylamine may be replaced by tritylamine or benzhydrylamine; these three compounds may also bear a methoxy group on one of the phenyl rings.

The compounds of formula (II), (IIa), (VII) and (VIIa) have a centre of asimmetry at the carbon atom linked to the amino group. Preparation of addition salts from said compounds and a chiral organic acid, preferably optically active mandelic acid, followed by fractional crystallization, may result in compounds which are enriched in one of the enantiomers and eventually in the optical resolution of the racemates leading to the two optically active forms. Optical resolution of these compounds may also be accomplished by specific chromatographic techniques.

Introduction of a N-protecting group R' is achieved by reacting the compound of formula (IIa) with a reactant suitable for protection of the amino groups as described, for instance, by M. Bodanszky et al. in Peptide Synthesis, 2nd Edition, John Wiley & Sons, 1976, p.18–49, Chapters 3 to 6.

As an example the Boc group may be introduced by reaction with di-tert-butyl-dicarbonate under basic conditions. The benzyloxycarbonyl group may be introduced by the general method described by E. C. Horning, in Organic Synthesis, Vol. III, Wiley, N.Y., 1955, p.167.

Accordingly, the compounds of formula (I) may be prepared, as an example, by protecting the amino group of 2-amino-7-hydroxytetralin (IIa) with a Boc group, by reaction of the aminotetralin (IIa) with di-tert-butyl-dicarbonate in an organic solvent such as dioxane or dimethylformamide, by treating the thus obtained product with a compound of formula (IIIa) or (IIIb) or (IIIc) under the above described conditions and by deprotecting the amino group by removal of the Boc group with trifluoroacetic acid according to following Scheme 2:

SCHEME 2

IIa ⟶

-continued
SCHEME 2

[Structure VIII: BocNH-tetralin-OH] —(IIIa) or (IIIb) or (IIIc)→

[Structure IX: BocNH-tetralin-O-Alk-COOR] —$CF_3COOH$→

[Structure I: $H_2N$-tetralin-O-Alk-COOR]

Removal of the protecting group Boc does not affect the carbalkoxy group or the molecule stereoconfiguration.

N-protection may also be carried out starting from the 7-methoxy-2-tetralone (V) through formation of a Schiff's base with an amine selected from benzylamine, tritylamine, and benzhydrylamine, optionally substituted on one of the phenyl rings with a methoxy group, followed by reduction with sodium borohydride.

Accordingly, as an example, the compounds of formula (I) wherein Alk represents an alkylene group as defined under (a) or (b) may be prepared starting from a 2-benzylamino-7-methoxytetralin of formula (VII) (Scheme 1), via demethylation with hydrobromic acid, reaction of the corresponding phenol with a compound of formula (IIIa) or (IIIb) under the above described conditions followed by debenzylation according to following Scheme 3:

SCHEME 3

VII —HBr 48%→

[Structure X: Ph-CH2NH-tetralin-OH] —(IIIa) or (IIIb)→

[Structure XI: Ph-CH2NH-tetralin-O-Alk-COOR] —$H_2$→ I

In Scheme 2, the Boc group may be replaced by the benzyloxycarbonyl group or any other N-protecting group as defined above. In Scheme 3 the benzyl group may be substituted on the benzene ring by a methoxy group or it may be replaced by a benzhydryl or trityl group optionally substituted with methoxy on one of the phenyl rings. Deprotection is carried out as described above.

The optically active forms of the compounds of formula (I) may be prepared according to known methods either by the process summarized in Scheme 2 starting from the optically active forms of the compound (IIa), or, by following the process sketched in Scheme 3 and resolving the racemate of the compound (VII), or its benzhydryl or trityl analog optionally substituted with methoxy, or by resolving the racemate of the compound of formula (I), for example by salification with an optically active acid, preferably optically active mandelic acid.

The N-protected 2-amino-7-hydroxytetralin carboxyalkyl ethers of formula (IV) as well as their salts are new compounds and represent the key intermediates in the synthesis of the compounds of formula (I). The present invention includes the individual isomeric forms of the compounds of formula (IV) as well as the mixtures thereof.

The 2-amino-7-hydroxytetralin carboxyalkyl ethers of formula (I) as well as their salts are useful as intermediates in the preparation of pharmacologically active compounds. As an example they may be employed in the preparation of phenylethanolaminotetralins which are endowed with a β-adrenergic receptor agonist activity selective towards the gastrointestinal tract and are suitable for the preparation of pharmaceutical compositions with spasmolytic activity.

Accordingly, a further specific object of the present invention is the use of the 2-amino-7-hydroxytetralin carboxyalkyl ethers of formula (I) in the preparation of the corresponding phenylethanolaminotetralins of formula (XII)

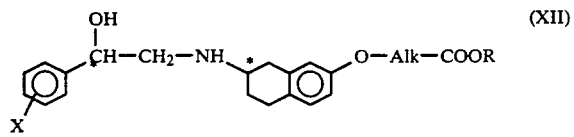

wherein X represents hydrogen, halogen, (C$_1$–C$_4$)alkyl, or trifluoromethyl, Alk and R are as defined above, and their pharmaceuticaly acceptable salts.

For the preparation of the phenylethanolaminotetralins (XII), the compounds of formula (I) may be reacted with a styrene oxyde of formula (XIII)

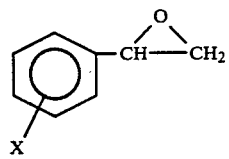

wherein X is as defined above, said styrene oxide being in the racemate or in an optically active form, or they may be reacted with a functional derivative of a mandelic acid of formula (XIV)

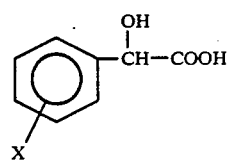

wherein X is as defined above, said mandelic acid (XIV) being in racemic or in optically active form, and the amide carbonyl group of the thus obtained intermediate mandelamide derivatives of formula (XV)

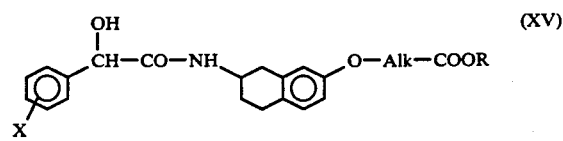

wherein X, R, and Alk are as defined above, may be reduced into a methylene group; the obtained compounds (XII) optionally being converted into the corresponding pharmaceutically acceptable salts.

The reaction between the compounds of formula (I) and the styrene oxides of formula (XIII) may be carried out with or without an inert, preferably polar, organic solvent and optionally in the presence of an equimolar amount of N-trimethylsilylacetamide to control the opening of the epoxyde. The reaction, which is generally complete in a few hours, typically 6 to 24 hours, may be carried out at room temperature or, preferably, at higher temperatures, typically from 50 to 90 C., to speed up the reaction course.

As "functional derivative" of the acid (XIV), the chloride, the anhydride, a mixed anhydride, an active ester, or a free acid suitably activated, for example with dicyclohexylcarbodiimide or benzotriazolyl-N-oxytris(-dimethylamino) phosphonium hexafluorophosphate (BOP) may conveniently be employed. A mandelic acid activated with a condensing agent such as BOP is preferably employed. The reaction between the functional derivative of a mandelic acid (XIV) and a compound (I) is generally carried out in an inert organic solvent such as methylene chloride, optionally in the presence of a proton acceptor such as triethylamine.

The obtained mandelamide (XV) is then reduced to the desired compound of formula (XII) by means of diborane or a reagent generating diborane such as the complex between borane and dimethylsulfide, commonly designated as "boranemethylsulfide". The reduction reaction is carried out in the presence of an organic solvent, e.g. tetrahydrofuran.

Independently on the method of synthesis, isolation and purification of the desired product (XII) are carried out according to well known conventional techniques.

It will be appreciated that the compounds of formula (XII) contain two centres of asymmetry at the carbon atoms marked with two asterisks in the above formula. In the preparation of these compounds the use of the single enantiomers of both reactants (I) and (XIII) or (I) and (XIV) will lead to the pure isomers of the compounds (XII). The reaction involved is stereoconservative and the same absolute configuration of the two chiral carbon atoms of reactants (I), (XIII), and (XIV), as assigned by the (R,S) convention, is maintained in the end compound of formula (XII). Using one of the reactants in racemic form will produce a mixture of two diastereoisomers while using both reactants in racemic form will afford a mixture of four stereoisomers. Fractional crystallization of the diastereoisomers or chromatography of the mixture may produce compounds which are enriched in one of the possible diastereoisomers or even a single stereoisomers.

The enantiomers of the compounds of formula (XII) wherein X, Alk, and R are as defined above, and their pharmaceutically acceptable salts, as well as the mixtures of enantiomers or diastereoisomers in any proportion represent therefore another object of the present invention.

A preferred group of compounds of formula (XII) comprises those compounds wherein X and R are as defined above and Alk represents a group —C($R_{10}R_{11}$)— or a group $Alk_1$ wherein $R_{10}$, $R_{11}$, and $Alk_1$ are as defined above, either as pure enantiomers or as mixtures of enantiomers or diastereosiomers in any proportion, and the pharmaceutically acceptable acid addition salts thereof.

An even more preferred group of compounds of formula (XII) comprises those compounds wherein X and R are as defined above and Alk represents a group —C($R_{10}R_{11}$)— wherein $R_{10}$ and $R_{11}$ represent methyl, either as the single enantiomers or as a mixture of enantiomers or diastereoisomers in any proportion, and the pharmaceutically acceptable acid addition salts thereof.

The compounds of formula (XII) have shown to be more potent, as $\beta$-receptor agonists, and/or more selective towards the gastrointestinal tract than the corresponding compound bearing an ethoxycarbonylmethoxy substituent at the 7-position of the tetralin moiety which has been described in EP-211721. They have a good activity on the intestinal motility and are useful as spasmolytics. Their toxicity is very low and compatible with their use as active ingredients in pharmaceutical compositions.

For their use as spasmolytics, the compounds of formula (XII) may be administered in a daily dosage of from 0.01 to 10 mg/kg of body weight of the mammal to be treated, depending on the route of administration, the type of treatment, whether curative or prophylactic, the age of the subject to be treated, and the severity of the disease. The compounds of formula (XII) are generally administered in unit dosage forms containing of form 0.1 to 150 mg, preferably from 1 to 50 mg, 1 to 5 times daily.

said unit doses are preferably formulated in pharmaceutical compositions wherein the active principle of formula (XII) is in admixture with a pharmaceutical carrier.

A further specific object of the present invention is therefore a pharmaceutical composition, comprising, as the active ingredient, a compound of formula (XII) or a pharmaceutically acceptable salt thereof, useful for the treatment of gastrointestinal diseases associated with a contraction of the smooth muscle.

Pharmaceutical compositions for use in the treatment or prophylaxis of gastrointestinal disorders may be formulated for the oral, sublingual, subcutaneous, intramuscular, intravenous, transdermal, or rectal administration route. Said pharmaceutical compositions can be prepared by conventional methods and using conventional ingredients or excipients as known in the field of industrial pharmacy.

It has also been found that the compounds of formula (XII) are useful for the treatment of ocular disorders, mainly for controlling intraocular pressure and for treating ocular hypertension and glaucoma.

The present invention also concerns, in another embodiment thereof, a method for treating ocular disorders, particularly for controlling intraocular pressure and for treating ocular hypertension and glaucoma in mammals, including humans, said method comprising administering to said mammals an effective amount of a compound of formula (XII) or of one of its pharmaceutically salts.

The invention also concerns the use of a compound of formula (XII) or of one of its pharmaceutically acceptable salts in combination with another active principle suited for the treatment of glaucoma. The active principle used in combination with the compound of formula (XII) may be an antiinflammatory agent, particularly a steroid or corticosteroid antiinflammatory agent used in the treatment of glaucoma, a side effect of which is an increase in intraocular pressure.

The present invention also concerns therefore a pharmaceutical composition containing a compound of formula (XII) or one of its pharmaceutically acceptable salts for controlling the increase in intraocular pressure following a treatment with steroid antiinflammatory agents. For their use in the treatment of ocular disorders, the compounds of formula (XII) are preferably formulated as ophthalmic pharmaceutical compositions to be administered topically to the eye, as solutions, suspensions or ointments.

Said ophthalmic compositions may contain from 0.00001 to 1% by wt., more particularly from 0.0001 to 0.2% by wt., of a compound of formula (XII). Each dosage unit (drop) contains from 10 ng to 1 mg, and preferably from 100 ng to 0.2 mg, of a compound of formula (XII).

These preparations may be administered by applying, in the eye, 1 or 2 drops, 1 to 3 times a day, to provide a daily posology of from 10 ng to 1 mg, preferably of from 100 ng to 0.2 mg of active principle.

The expression "controlling elevated intraocular pressure", as used herein, stands for normalizing, reducing and modulating high intraocular pressure (IOP) which is the earliest symptom in the diagnosis of glaucoma. The expression also means that the reduction in intraocular pressure obtained by the use of a compound of formula (XII) or of one of its pharmaceutically acceptable salts lasts for a period of time sufficiently long, for instance inbetween two consecutive administrations.

The IOP lowering effect of a compound of formula (XII) may be evaluated in animals, as an example in the rabbit, by means of a test which involves oral administration of large amounts of water, such as that described in Arch. Ophthal., 1969, 82, 381-384, or in J. Ocul. Pharmacol., 1985, 1(2), 161-168; or rapid i.v. injection of a glucose solution, such as that described in Boll. Ocul., 1979, 58(7-8), 359-66.

To obtain suitable preparations, the pharmaceutical compositions for ophthalmic use may be admixed with a carrier acceptable for a topical ophthalmic administration or for a systemic treatment. As pharmaceutical carriers acceptable for an ophthalmic topical administration, there may be cited water, mixtures of water and water-miscible solvents such as lower alkanols, vegetable oils, mineral oils which may contain from 0.5 to 5% by wt. of hydroxyethylcellulose, ethyl oleate, carboxymethylcellulose, polyvinylpyrrolidone, and other water-soluble polymers, which are non toxic and compatible with an ophthalmic use, as an example cellulose derivatives, such as methylcellulose, carboxymethylcellulose alkali metal salts, hydroxymethylcellulose, hydroxyethylcellulose, hydroxypropylmethylcellulose, acrylates, such as polyacrylic acid salts, ethylpolyacrylates, polyacrylamides, natural products such as gelatin, alginates, pectines, tragacanth, karaya gum, chondrus, agar, acacia, starch derivatives such as starch acetate, hydroxyethyl starch ethers, hydroxypropyl starch, as well as other synthetic derivatives such as polyvinylalcohol, polyvinylpyrrolidone, polyvinylmethylether, polyethylene oxide, neutral carbopol, or xanthan, and their mixtures.

The pharmaceutical preparations for ophthalmic use may also contain non-toxic auxiliary substances such as emulsifying, preserving, wetting, bodying agents and the like such as for instance polyethylene glycols 200, 300, 400, 600, carbowaxes 1000, 1500, 4000, 6000, 10000, antibacterial agents such as quaternary ammonium compounds, phenylmercuric salts known to have cold sterilizing properties and which are non-injurious in use, thimerosal, propylparaben, benzyl alcohol, phenyl ethanol, buffering agents, buffering agents such as alkali metal chlorides, borate, acetate, or gluconate buffers, antioxidants such as sodium metabisulfite, butyrated hydroxyanisole, butyrated hydroxytoluene, or the like agents and other agents typically used in this field such as sorbitan monolaurate, triethanolamine oleate, polyoxyethylene sorbitan monopalmitate, dioctyl alkali metal sulfosuccinate, monothioglycerol, ethylenediamine tetraacetic acid and the like.

Additionally, suitable ophthalmic excipients may be employed such as for instance phosphate buffer, isotonic boric acid, isotonic alkaline chloride solutions or tromethamine.

The pharmaceutical preparations for ophthalmic use may also be in the form of a suspension wherein the soluble particles are water-soluble or insoluble polymers. Such a suspension may contain microparticles or nanoparticles.

The compositions for ophthalmic use according to the invention may contain additional active principles. Accordingly, antibiotics, anesthetics or other IOP lowering agents may be present.

The following examples further illustrate the invention without however limiting it.

PREPARATION I 2-amino-7-hydroxytetralin hydrobromide.

(a) A mixture of 7-methoxy-2-tetralone (8 g), benzylamine (4.8 g), anhydrous toluene (150 ml) and p-toluenesulfonic acid (100 mg) is refluxed for 3 hours and then evaporated to dryness. The oily residue is taken up in methanol (100 ml) and sodium borohydride (8.5 g) is cautiously added to the obtained solution kept at 0–5 C. The reaction mixture is then stirred overnight at room temperature, water (50 ml) is added thereto and the mixture is stirred again for 30 minutes. The solvent is evaporated off and the residue is taken up in a mixture of water (30 ml) and concentrated ammonium hydroxide (10 ml). The reaction mixture is extracted with ethyl acetate (200 ml), the organic phase is dried over sodium sulfate, filtered and evaporated to dryness. A dark oil is obtained which is purified by flash chromatography eluting with a mixture ethyl acetate/methanol 95/5. The obtained free base is converted into the corresponding hydrochloride by dissolving it in isopropanol (40 ml) and adding hydrochloric acid saturated isopropanol thereto. 2-Benzylamino-7-methoxytetralin hydrochloride (11.4 g) is thus obtained. M.p. 265°–267° C. (dec.).

(b) The above product, dissolved in methanol (200 ml) and water (100 ml), is hydrogenated in the presence of 10% Pd/C (1.2 g), at a temperature of 45°–50° C. and atmospheric pressure. After 4 hours the catalyst is filtered off, the filtrate is evaporated to dryness and the obtained residue is twice taken up in absolute ethanol and evaporated to dryness. A white solid is obtained which is taken up in hot isopropanol (70 ml). Upon cooling a precipitate is obtained of 2-amino-7-methoxytetralin hydrochloride (7.8 g). M.p. 214°–216° C.

(c) A suspension of the compound obtained in step (b) (6.6 g) in 48% hydrobromic acid (80 ml) is refluxed for 2 hours. The obtained solution is evaporated to dryness and the residue is twice taken up in absolute ethanol and concentrated to dryness. An oily product is thus obtained which is dissolved in hot isopropanol (20 ml). Ethyl ether (30 ml) is added thereto and a crystalline precipitate of 2-amino-7-hydroxytetralin hydrobromide (6.8 g) is obtained. M.p. 171°–173° C.

PREPARATION II

R-2-amino-7-hydroxytetralin monohydrate

A solution of (+) mandelic acid (43 g) in absolute ethanol (550 ml) is added to a solution of raw 2-amino-7-methoxytetralin free base (50 g) in absolute ethanol (550 ml) (said free base being obtained from the corresponding hydrochloride described in Preparation I step (b) by neutralization with 10% sodium hydroxide followed by extraction with ethyl acetate and evaporation of the organic solvent). The reaction mixture is kept at room temperature overnight, the obtained precipitate is recovered by filtration and crystallized twice from absolute ethanol, recovering the product which crystallizes upon standing overnight at room temperature. The addition salt of (+) 2-amino-7-methoxytetralin with (+) mandelic acid (34.2 g, 74%) is thus obtained. M.p. 190°–192° C.

(The mother liquors of the first crystallization are separately recovered and employed in Preparation III below.)

The obtained salt (34 g) is suspended in water (300 ml) and the reaction mixture is made basic by the addition of 1N sodium hydroxide. The (+) 2-amino-7-methoxytetralin free base is extracted therefrom with ethyl acetate, the organic solvent is evaporated off and the residue is taken up in 48% hydrobromic acid (260 ml). The reaction mixture is heated to the reflux temperature for 3 hours and then concentrated to dryness under vacuum. The residue is taken up in water (70 ml), the aqueous solution is basified by the addition of concentrated ammonium hydroxide, and cooled overnight; the precipitate is recovered by filtration yielding R-2-amino-7-hydroxytetralin monohydrate (17 g). M.p. 143°–144° C.; $[\alpha]_D^{20} = +85.1°$(c=0.5% in methanol). The corresponding hydrochloride has a rotatory power which correponds to that reported in the literature (Molecular Pharmacology, 1982, 22, 281–289).

PREPARATION III

S-2-amino-7-hydroxytetralin monohydrate

The mother liquors of the first crystallization of the product of Preparation II, which contain the salt of (−) 2-amino-7-methoxytetralin with (+) mandelic acid, are evaporated to dryness, the residue is suspended in water (300 ml) and the reaction mixture is made basic by the addition of 1N sodium hydroxide. The free base is extracted with ethyl acetate and the organic solution is then processed as described in Preparation II but using (−) mandelic acid instead of (+) mandelic acid, the yielding the addition salt of (−) 2-amino-7-methoxytetralin with (−) mandelic acid (M.p. 189°–191° C.) which is neutralized and demethylated with HBr, affording S-2-amino-7-hydroxytetralin monohydrate (17 g). M.p. 143°–144° C.; $[\alpha]_D^{20} = -86.9°(c=0.5\%$ in methanol).

The corresponding hydrochloride has a rotatory power which corresponds to that reported in the literature (Molecular Pharmacology, 1982, 22, 281–289).

PREPARATION IV 2-benzylamino-7-hydroxytetralin

A mixture of 2-benzylamino-7-methoxytetralin hydrochloride (25 g) described in Preparation I step (a), and 33% hydrobromic acid in acetic acid (215 ml) in the presence of 48% hydrobromic acid (36 ml) is refluxed, under stirring, for 2 hours. The reaction mixture is then concentrated to dryness under reduced pressure and the residue is taken up in absolute ethanol (100 ml) and concentrated to dryness. The step of taking up in absolute ethanol and concentrating to dryness is repeated two other times and the thus obtained product is finally triturated with acetone (150 ml) and filtered yielding 2-benzylamino-7-hydroxytetralin hydrobromide (25.3 g). M.p. 198°–200° C. This product is then dissolved in hot water (1300 ml), the solution is cooled and concentrated ammonium hydroxide is then added thereto. The free base is extracted with ethyl acetate, the organic solution is dried and the solvent is evaporated off yielding a solid which is crystallized from toluene (250 ml). 2-Benzylamino-7-hydroxytetralin free base (14 g) is thus obtained. M.p. 161°–163° C.

PREPARATION V

S-2-benzylamino-7-methoxytetralin hydrochloride

A solution of (−) mandelic acid (24.5 g) in absolute ethanol (150 ml) is added to a solution of 2-benzylamino-7-methoxytetralin free base (44 g), described in Preparation I, step (a), in absolute ethanol (140 ml). The precipitate which forms upon standing at room temperature overnight is recovered by filtration, washed and crystallized twice from absolute ethanol (250 ml) yielding the addition salt of (−) 2-benzylamino-7-methoxytetralin with (−) mandelic acid (33 g). M.p. 155°–157° C. $[\alpha]_{365}^{20} = -316°(c=1\%$ in methanol).

(The mother liquors from the first crystallization are recovered separately and employed in Preparation VII below.)

The obtained salt (30 g) is dissolved in water (400 ml) and the aqueous solution is basified by the addition of 32% ammonium hydroxide. The free base is extracted with ethyl acetate, the organic extract is washed with water, dried over sodium sulfate and concentrated to dryness affording an oily product (20 g) which is dissolved in isopropanol. Upon the addition of hydrogen chloride saturated isopropanol, a precipitate forms which is recovered by filtration, dried (22 g) and crystallized twice from a mixture methanol/water 1/1 yielding the compound of the title, S-2-benzylamino-7-methoxytetralin hydrochloride. M.p. 287°–290° C. $[\alpha]_{365}^{20} = -231°(c=1\%$ in methanol).

Absolute configuration of this compound (S) has been assigned by removing the N-benzyl group and comparing the rotatory power of the thus obtained product with that known in the literature.

PREPARATION VI

S-2-benzylamino-7-hydroxytetralin hydrobromide

A solution of S-2-benzylamino-7-methoxytetralin hydrochloride (15 g) in a mixture of 33% hydrobromic acid in acetic acid (100 ml) and 48% hydrobromic acid (100 ml) is refluxed under stirring for 3 hours. The obtained solution is evaporated to dryness under reduced pressure and the residue is taken up in absolute ethanol and the ethanol solution is evaporated to dryness. The step of taking up the residue in absolute ethanol and concentrating to dryness the ethanol solution is repeated three times. The oily residue thus obtained is dissolved in hot acetone and crystallized therefrom. The precipitate is recovered by filtration, washed with acetone and ethyl ether and dried yielding S-2-benzylamino-7-hydroxytetralin hydrobromide (17 g). M.p. 198°–202° C. $[\alpha]_{365}^{20} = -201.7°(c=1\%$ in methanol).

PREPARATION VII

R-2-benzylamino-7-methoxytetralin hydrochloride

The mother liquors from the first crystallization of the addition salt of (−) 2-benzylamino-7-methoxytetralin with (−) mandelic acid (Preparation V) are concentrated to dryness and the obtained residue is dissolved in water (400 ml). The aqueous solution is basified by the addition of 32% ammonium hydroxide and the free base is extracted therefrom with ethyl acetate. The organic extract is washed with water, dried over sodium sulfate and concentrated to dryness. The residue is dissolved in ethanol and a solution of (+) mandelic acid (12.5 g) in absolute ethanol (75 ml) is added thereto. The precipitate which forms upon standing at room temperature overnight is recovered by filtration, washed and crystallized three times from absolute ethanol yielding the addition salt of (+) 2-benzylamino-7-methoxytetralin with (+) mandelic acid (24 g). M.p. 152°–154° C. $[\alpha]_{365}^{20} = +309°(c=1\%$ in methanol).

The obtained salt (20 g) is dissolved in water (300 ml) and the aqueous solution is basified by the addition of 32% ammonium hydroxide. The free base is extracted with ethyl acetate, the organic extract is washed with water, dried over sodium sulfate and concentrated to dryness. The residue is dissolved in isopropanol and hydrogen chloride saturated isopropanol is then added thereto to precipitate raw R-2-benzylamino-7-methoxytetralin hydrochloride which is recovered by filtration, dried and crystallized twice from a mixture methanol/water 1/1. M.p. 278°–282° C. $[\alpha]_{365}^{20} = +229.9°(c=1\%$ in methanol).

PREPARATION VIII

R-2-benzylamino-7-hydroxytetralin hydrobromide

A solution of R-2-benzylamino-7-methoxytetralin hydrochloride (15 g) in a mixture of 33% hydrobromic acid in acetic acid (100 ml) and 48% hydrobromic acid (100 ml) is refluxed under stirring for 3 hours. The obtained solution is evaporated to dryness under reduced pressure and the residue is taken up in absolute ethanol and the ethanol solution is evaporated to dryness. The step of taking up the residue in absolute ethanol and concentrating to dryness the ethanol solution is repeated three times. The obtained residue is dissolved in hot acetone and crystallized therefrom. The precipitate is recovered by filtration, washed with acetone and ethyl ether and dried yielding R-2-benzylamino-7-hydroxytetralin hydrobromide (15.5 g).

M.p. 198°–202° C. $[\alpha]_{365}^{20} = +198.4°(c=1\%$ in methanol).

Example 1

2-benzylamino-7-(ethoxycarbonylpentan-5-yloxy)tetralin hydrochloride

A mixture of 2-benzylamino-7-hydroxytetralin free base (8 g), described in Preparation IV, and 55% sodium hydride (1.7 g) in toluene (250 ml) is maintained under a nitrogen stream and heated to 70° C. for 30 minutes. The reaction mixture is allowed to cool to room temperature and a mixture of 6-bromohexanoic acid ethyl ester (10.5 g) and tetrabutylammonium bromide (0.5 g) in toluene (200 ml) is slowly dripped in. After refluxing for 8 hours, the reaction mixture is cooled to room temperature and water (100 ml) is added thereto. The organic phase is separated, washed with 3N sodium hydroxide, dried and concentrated to dryness. The obtained residue is dissolved in isopropanol and hydrogen chloride saturated isopropanol is then added thereto to precipitate the compound of the title(8.9 g) M.p. 140°–142° C.

Example 2

2-amino-7-(ethoxycarbonylpentan-5-yloxy)tetralin hydrochloride

A solution of 2-benzylamino-7-(ethoxycarbonylpentan-5-yloxy) tetralin hydrochloride (8.9 g), prepared as described in Example 1, in 95% ethanol (150 ml) is hydrogenated at atmospheric pressure and 60° C. in the presence of 10% Pd/C (1 g) as the hydrogenation catalyst. After 3 hours the catalyst is filtered off, the filtrate is concentrated to dryness and the residue is twice taken up in absolute ethanol (100 ml) and concentrated to dryness. The obtained product is then triturated with acetone (100 ml), filtered and crystallized from isopropanol (50 ml) affording 5.5 g of the compound indicated in the title. M.p. 114°–117° C.

Example 3

2-benzylamino-7-(ethoxycarbonylpropan-3-yloxy)tetralin hydrochloride

A mixture of 2-benzylamino-7-hydroxytetralin free base (15 g), described in Preparation IV, and 95% sodium hydride (2.8 g) in toluene (400 ml), maintained under a nitrogen stream, is heated to 70° C. for 30 minutes. The reaction mixture is allowed to cool to room temperature and a mixture of 4-bromobutanoic acid ethyl ester (9.2 ml) and tetrabutylainmonium bromide (0.5 g) in toluene (200 ml) is slowly dripped in. After heating at 90° C. for 8 hours, the reaction mixture is cooled to room temperature and extracted twice with ethyl ether (100 ml). The organic phase is washed with a mixture of 0.1N sodium hydroxide and water and concentrated to dryness. The residue is dissolved in isopropanol (100 ml), activated charcoal is added to the obtained solution and the suspension is filtered. The filtrate is acidified by the addition of hydrogen chloride saturated isopropanol to precipitate the compound of the title (14 g) M.p. 175°–177° C.

Example 4

2-amino-7-(ethoxycarbonylpropan-3-yloxy)tetralin hydrochloride

A solution of 2-benzylamino-7-(ethoxycarbonylpropan-3-yloxy) tetralin hydrochloride (14 g), prepared as described in Example 3, in a mixture of 95% ethanol (250 ml) and water (10 ml) is hydrogenated at atmospheric pressure and 60° C. in the presence of 10% Pd/C (2 g) as the hydrogenation catalyst. After 5 hours the catalyst is filtered off, the filtrate is concentrated to dryness and the residue is taken up in absolute ethanol (100 ml) and concentrated to dryness a few times. The obtained product is then triturated with acetone, filtered and crystallized from isopropanol affording 8.8 g of the compound of the title. M.p. 134°–136° C.

Example 5

2-benzylamino-7-(ethoxycarbonylbutan-4-yloxy)tetralin hydrochloride A solution of 2-benzylamino-7-hydroxytetralin free base (10 g), prepared as described in Preparation IV, and 80% sodium hydride (1.6 g) in dimethylsulfoxide (140 ml) is stirred-at room temperature, under a nitrogen stream, for 30 minutes. A catalytic amount of potassium iodide and 5-bromovaleric acid ethyl ester (10.45 g) are added to the reaction mixture and stirring at room temperature is continued for 17 hours. Ice/water (400 ml) is then added thereto and the reaction mixture is extracted with ethyl acetate. The organic phase is washed with 2N NaOH and then with water, dried over sodium sulfate and concentrated to dryness under vacuum. The residue is dissolved in isopropanol and the compound of the title is precipitated from the obtained solution by the addition of hydrogen chloride saturated isopropanol and crystallized from isopropanol (100 ml). Yield: 10.7 g. M.p. 154°–156° C.

Example 6

2-amino-7-(ethoxycarbonylbutan-4-yloxy)tetralin hydrochloride

A solution of 2-benzylamino-7-(ethoxycarbonylbutan-4-yloxy)tetralin hydrochloride (10.7 g), prepared as described in Example 5, in 95% ethanol (250 ml) and water (25 ml) is hydrogenated at 60° C. and atmospheric pressure using 10% Pd/C (1.2 g) as the hydrogenation catalyst. After 6 hours the catalyst is filtered off, the filtrate is concentrated and the residue is taken up in absolute ethanol and concentrated to dryness a few times. The obtained product is then triturated with ethyl ether and filtered. The residue is crystallized from isopropanol yielding 8 g of the compound indicated in the title. M.p. 131°–133° C.

Example 7

2-Benzylamino-7-(2-carboxy-propan-2-yloxy)tetralin and

2-Benzylamino-7-(2-ethoxycarbonyl-propan-2-yloxy)-tetralin oxalate A solution of 2-benzylamino-7-hydroxytetralin free base (19 g) prepared as described in Preparation IV and 1,1,1-trichloro-2-methyl-2-propanol (26.6 g) in acetone (500 ml) is stirred at room temperature for 15 minutes. The reaction mixture is then cooled to 15° C., potassium hydroxide (10.9-g) is added thereto and the reaction mixture is stirred at room temperature for 2 hours. Two additional portions of potassium hydroxide (10.9 g + 10.9 g) are then added thereto and the obtained reaction mixture is stirred at room temperature overnight, and then concentrated to dryness under reduced pressure. Ice/water (250 ml) is the added and the solution is washed with ethyl ether, decolorized with activated charcoal and acidified by the addition of HCl up to pH 5–6. The precipitated 2-benzylamino-7-(2-carboxy-propan-2-yloxy)tetralin is recovered by filtration (14 g) and added to a solution of thionyl chloride (3.6 ml) in absolute ethanol (100 ml). The mixture is heated to the reflux temperature for 4 hours and then concentrated to dryness. A mixture of ice/water is added thereto and the solution is made basic by the addition of ammonium hydroxide. The solution is extracted with ethyl acetate, the organic extract is dried and concentrated to dryness. The obtained free base is dissolved in acetone and oxalic acid is added thereto. The precipitate is recovered by filtration and crystallized from 95% ethanol (180 ml), yielding 11.3 g of 2-benzylamino-7-(2-ethoxycarbonyl-propan-2-yloxy)tetralin oxalate. M.p. 174°–176° C. A small sample of the above obtained 2-benzylamino-7-(2-carboxy-propan-2-yloxy)tetralin has been washed with water, treated with acetone and dried. M.p.240°–242° C. Hydrogenation of said acid by the procedure described in Example 2 affords the corresponding deprotected 2-amino-7-(2-carboxypropan-2-yloxy)tetralin.

Example 8

2-amino-7-(2-ethoxycarbonylpropan-2-yloxy)tetralin oxalate A solution of 2-benzylamino-7-(2-ethoxycarbonyl-propan-2-yloxy)tetralin free base (9.1 g), prepared as described in Example 7, in 95% ethanol (100 ml) and hydrochloric acid (4 ml) is hydrogenated at 60° C. and atmospheric pressure using 10% Pd/C (1 g) as the hydrogenation catalyst. After 4 hours the catalyst is filtered off, the filtrate is concentrated and the residue is taken up in absolute ethanol and concentrated to dryness a few times. The obtained product is then dissolved in diluted ammonium hydroxide and extracted with ethyl ether. The organic phase is dried and concentrated to dryness and the residue is purified by flash chromatography eluting with a mixture methylene chloride/ethanol 8/2. The fractions containing the desired product are pooled together and concentrated to dryness. The residue is dissolved in acetone and oxalic acid is added to precipitate the compound of the title which is then crystallized from acetone (10 ml) yielding 0.66 g. M.p. 140°–14220 C.

Example 9

S-2-Benzylamino-7-(2-ethoxycarbonylpropan-2-yloxy)-tetralin hydrochloride

The compound of the title has been prepared by following substantially the same procedure as in Example 7 but starting from S-2-benzylamino-7-hydroxytetralin free base (prepared from the corresponding hydrobromide described in Preparation VII by dissolving the hydrobromide in water, basifying the aqueous solution by the addition of concentrated ammonium hydroxide, extracting the free base with ethyl acetate and evaporating off the organic solvent). u At the end of this procedure, the free base so obtained is dissolved in isopropanol and isopropanol saturated with hydrochloric acid is added to precipitate the hydrochloride which is separated by filtration and crystallized from isopropanol. $[\alpha]_{365}^{20} - 156.2°(c=0.5\%$ in methanol). M.p. 152°–154° C.

Example 10

R-2-Benzylamino-7-(2-ethoxycarbo an-2-yloxy)tetralin

The compound of the title has been prepared by following substantially the same procedure as in Example 7 but starting from R-2-benzylamino-7-hydroxytetralin free base (prepared from the corresponding hydrobromide described in Preparation VIII by dissolving the hydrobromide in water, basifying the aqueous solution by the addition of concentrated ammonium hydroxide, extracting the free base with ethyl acetate and evaporating off the organic solvent). At the end of this procedure, the free base so obtained is dissolved in isopropanol and isopropanol saturated with hydrochloric acid is added to precipitate the hydrochloride which is separated by filtration and crystallized from isopropanol. $[\alpha]_{365}^{20} = +158.4°(c=0.5\%$ in methanol); M.p.148°–150° C.

Example 11

S-2-amino-7-(2-ethoxycarbonylpropan-2-yloxy)tetralin oxalate

The compound of the title has been prepared by following substantially the same procedure as in Example 8 but starting from the compound obtained in Example 9.

$[\alpha]_{365}^{20} = -140.4°(c=1\%$ in methanol; M.p. 132°–134° C.

Example 12

R-2-amino-7-(2-ethoxycarbonylpropan-2-yloxy)tetralin oxalate

The compound of the title has been prepared by following substantially the same procedure as in Example 8 but starting from the compound obtained in Example 10.

$[\alpha]_{365}^{20} = +140.0°(c=1\%$ in methanol); M.p. 131°–134° C.

Example 13

N-[7-ethoxycarbonylbutan-4-yloxy)-1,2,3,4-tetrahydronaphth-2-yl]-2-hydroxy-2-(3-chlorophenyl) ethanamine hydrochloride A solution of 2-amino-7-(ethoxycarbonylbutan-4-yloxy)tetralin free base (5 g) (obtained by dissolving the corresponding hydrochloride, prepared as described in Example 6, in water, making the aqueous solution basic by the addition of concentrated ammonium hydroxide, extracting the free base with ethyl acetate and evaporating off the solvent) and 3-chlorostyrene oxide (4.6 g) in anhydrous dimethylsulfoxide (15 ml) is heated to 80° C. under stirring and under a nitrogen stream, for 11 hours. After standing at room temperature overnight the reaction mixture is poured into a mixture ice/water and extracted with ethyl acetate. The organic phase is washed with water, dried over sodium sulfate and concentrated to dryness. The obtained residue is dissolved in ethyl ether and hydrogen chloride saturated isopropanol is added thereto. The precipitate is recovered by filtration, dried and crystallized twice from isopropanol (40 ml) affording 3.9 g of the compound of the title. M.p. 127°–130° C.

Example 14

N-[7-(ethoxycarbonylpentan-5-yloxy)-1,2,3,4-tetrahydronaphth-2-yl]2-hydroxy-2-(3-chlorophenyl) ethanamine hydrochloride A solution of 2-amino-7-(ethoxycarbonylpentan-5-yloxy)tetralin free base (4.2 g), obtained from the corresponding hydrochloride, prepared as described in Example 2, by neutralization and trimethylsilylacetamide (2.4 g) in anhydrous dimethylsulfoxide (10 ml) is stirred at 25° C. for 20 minutes. 3-Chlorostyrene oxide (3.6 g) is then added thereto and the reaction mixture is heated to 80°0 C. for 9 hours and then poured into water (100 ml) containing concentrated hydrochloric acid (3 ml). Ethyl acetate (50 ml) is added and the obtained mixture is stirred for 1 hour. The aqueous phase is separated and washed with ethyl acetate (2×50 ml); the organic washings are combined with the separated organic phase, washed with water, diluted ammonium hydroxide, and water. The washed organic phase is then dried and concentrated to dryness. The residue is purified by flash chromatography eluting with ethyl acetate. The product obtained by evaporating off the solvent in the recovered fractions is dissolved in isopropyl ether (100 ml) and hydrogen chloride saturated isopropanol is then added thereto. The oily product which separates solidifies upon standing and is therefore recovered by filtration (3.9 g). Crystallization from isopropanol (20 ml) affords 2 g of the compound of the title. M.p. 109°–112° C.

Example 15

N-[7-(ethoxycarbonylpropan-3-yloxy)-1,2,3,4-tetrahydronaphth-2-yl]-2-hydroxy-2-(3-chloro phenyl)ethanamine hydrochloride A mixture of 2-amino-7-(ethoxycarbonylpropan-3-yloxy)tetralin free base (5.3 g), obtained by neutralization of the corresponding hydrochloride, prepared as described in Example 4, and N-trimethylsilylacetamide (2.75 g) in anhydrous dimethylsulfoxide (10 ml) is charged into a reaction vessel under anhydrous conditions and kept at 25° C. for 20 minutes under a nitrogen stream. 3-Chlorostyrene oxide (3 g) is then added thereto and the reaction mixture is heated to 60° C. for 7 hours. After standing at room temperature overnight, the reaction mixture is poured into water and extracted with ethyl acetate. The organic phase is thoroughly washed with water, dried and concentrated to dryness. The obtained residue is dissolved in isopropanol and hydrogen chloride saturated isopropanol is then added thereto. The precipitate is recovered by filtration and crystallized from isopropanol (80 ml) yielding 4.4 g of the compound of the title. M.p. 156°–158° C.

Example 16

N-[7-(2-ethoxycarbonyl-propan-2-yloxy)-1,2,3,4-tetrahydronaphth-2-yl]-2-hydroxy-2-(3-chlorophenyl)ethanamine hydrochloride A mixture of 2-amino-7-(2-ethoxycarbonyl-propan-2-yloxy)-tetralin free base (3.2 g), obtained by neutralization of the corresponding oxalate prepared as described in Example 8 and N-trimethylsilylacetamide (2.5 g) in anhydrous dimethylsulfoxide (10 ml) is stirred at room temperature, under a nitrogen stream and anhydrous conditions for 20 minutes. 3-chlorostyrene oxide (2.8 g) is then added thereto and the reaction mixture is heated to 80° C. for 8 hours, allowed to stand at room temperature overnight, treated with an additional amount of 3-chlorostyrene oxide (1.0 g), heated to 80° C. for further 5 hours and then poured into ice/water (150 ml). Concentrated hydrochloric acid (a few mls) and ethyl acetate (100 ml) are added thereto and the obtained mixture is stirred at room temperature for 1 hour. The two phases are separated, the aqueous one is washed with ethyl acetate (2×50 ml) and the organic washings are combined with the separated organic phase, washed sequentially with water, diluted ammonium hydroxide, and water, dried and concentrated to dryness yielding an oily product (6.6 g) which is purified by flash chromatography eluting with ethyl acetate. The thus purified product is converted into the corresponding hydrochloride by dissolving it in isopropyl ether and making the obtained solution acidic by the addition of hydrogen chloride saturated isopropanol. Upon standing a precipitate forms which is recovered by filtration and crystallized twice from isopropyl alcohol affording 1 g of the compound of the title. M.p. 142°–144° C.

Example 17

N-[(2S)-7-(2-ethoxycarbonyl-propan-2-yloxy)-1,2,3,4-tetrahydronaphth-2-yl]-(2R)-2-hy droxy-2-(3-chlorophenyl)ethanamine hydrochloride The compound of the title has been prepared by following substantially the same procedure as in Example 16 but starting from (R)-3-chlorostyrene oxide and S-2-amino-7-(2-ethoxycarbonylpropan-2-yloxy)tetralin free base obtain by neutralization of the corresponding oxalate prepared in Example 11.
$[\alpha]_{365}^{20} = -270°(c=1\%$ in methanol); M.p.=206°–208° C.

Example 18

N-[(2R)-7-(2-ethoxycarbonyl-propan-2-yloxy)-1,2,3,4-tetrahydronaphth-2-yl]-(2R)-2-hyd roxy-2-(3-chlorophenyl)ethanamine hydrochloride The compound of the title has been prepared by following substantially the same procedure as in Example 16 but starting from (R)-3-chlorostyrene oxide and R-2-amino-7-(2-ethoxycarbonylpropan-2-yloxy)tetralin free base obtain by neutralization of the corresponding oxalate prepared in Example 12.
$[\alpha]_{365}^{20} = +125.7°(c=1\%$ in methanol) M.p. 109°–112° C.

The compounds of Examples 13 and 16 have been evaluated in the isolated rat colon test, carried out according to the method described in EP-A-255415. The activity of said compounds expressed as $IC_{50}$, shown to be higher than that of N-[7-(ethoxycarbonylmethoxy)-1,2,3,4-tetrahydronaphth-2-yl]-2-hydroxy-2-(3-chlorophenyl) ethanamine oxalate described in Example 11 of EP-A-211721.

The pharmacological activity of some representative compounds of formula (XII) on intraocular pressure (IOP), has been evaluated in rabbits, using the experimental glaucoma model developed by L. Bonomi (1976).

In this model a rapid increase in the IOP is elicited in rabbits by fast i.v. injection of 15 mg/Kg of a 5% glucose solution. The IOP reaches its maximum (29±1.6 mmHg) in 5 minutes, then it gradually returns to its almost normal value (22±1.6 mmHg in 40 minutes.

Females, Fauve de Bourgogne, pigmented rabbits (3–4 Kg) with a normal basal IOP at both eyes (19±0.6 mmHg) are employed in this test. They were instilled a single dose of 50 μl of an eye solution (either containing one of the products to be tested in physiological solution or the vehicle alone) in one eye, in blind (the other eye remained untreated and served as control). Ten minutes after this instillation, a second IOP measurement was done, and immediately after this measurement 15 mg/Kg of a 5% glucose solution was rapidly injected in the ear marginal vein. IOP measurements were then done 5, 10, 20, 30 and 40 minutes after the injection. IOPS were taken with a pneumotonometer. While instillation of the vehicle did not give raise to any significative difference in the IOP elevation curve, with respect to that of the untreated eyes, the results obtained with some representative compounds of formula (XII), and more particularly with the compounds of examples 13 and 16, show that the compounds of formula (XII) are active on this model of acute glaucoma.

We claim:

1. A 2-amino-7-hydroxytetralin carboxyalkyl ether of formula (I)

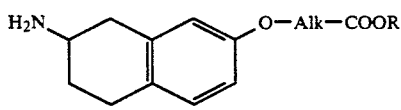 (I)

wherein Alk represents a straight or branched $(C_3-C_5)$-alkylene chain, and R represents hydrogen or $(C_1-C_4)$-alkyl or a salt thereof.

2. A compound according to claim 1 wherein Alk represents (a) a group 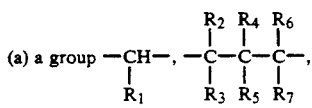

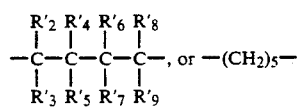, or $-(CH_2)_5-$ wherein
$R_1$ is ethyl, propyl or butyl,
$R_2$ to $R_7$ are all hydrogen atoms or one of $R_2$ to $R_7$ is a methyl or ethyl group and the others are hydrogen atoms, or two of $R_2$ to $R_7$ are methyl groups and the others are hydrogen atoms
$R'_2$ to $R'_9$ are all hydrogen atoms or one of $R'_2$ to $R'_9$ is a methyl group and the others are hydrogen atoms;

b) a group 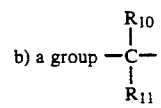

wherein
$R_{10}$ and $R_{11}$ are independently methyl or ethyl or $R_{11}$ is also propyl when $R_{10}$ is methyl;

c) a group 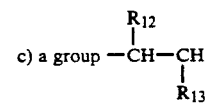

wherein one of $R_{12}$ and $R_{13}$ is hydrogen and the other is methyl, ethyl or propyl, or one of $R_{12}$ and $R_{13}$ is methyl and the other is methyl or ethyl.

3. A compound according to claim 2 wherein Alk represents a group 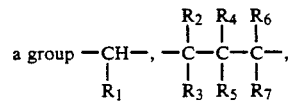

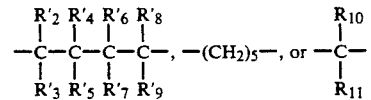

wherein $R_1$ to $R_{11}$ are as defined in claim 2.

4. A compound according to claim 3 which is selected from the group consisting of 2-amino-7-(ethoxycarbonyl-propan-3-yloxy)tetralin, 2-amino-7-(ethoxycarbonylbutan-4-yloxy)tetralin, 2-amino-7-(ethoxycarbonylpentan-5-yloxy)tetralin, 2-amino-7-(2-ethoxycarbonylpropan-2-yloxy)tetralin, and salts thereof.

* * * * *